United States Patent
Wohlgemuth et al.

(10) Patent No.: US 11,304,854 B2
(45) Date of Patent: *Apr. 19, 2022

(54) BUFFERED ADHESIVE COMPOSITIONS FOR SKIN-ADHERING MEDICAL PRODUCTS

(71) Applicant: HOLLISTER INCORPORATED, Libertyville, IL (US)

(72) Inventors: Jan Wohlgemuth, Horsholm (DK); Mette Maack, Lyngby (DK); Carsten Rikhof, Lexington, VA (US); Peter Skov, Aalsgaarde (DK); Kristoffer Nielsen, Graested (DK); Per Ladefoged, Gundsomagle (DK); Kenneth Nielsen, Alsgarde (DK); Michael Taylor, Mundelein, IL (US); Richard Murahata, Libertyville, IL (US)

(73) Assignee: HOLLISTER INCORPORATED, Libertyville, IL (US)

(*) Notice: Subject to any disclaimer, the term of this patent is extended or adjusted under 35 U.S.C. 154(b) by 41 days.

This patent is subject to a terminal disclaimer.

(21) Appl. No.: 16/594,665

(22) Filed: Oct. 7, 2019

(65) Prior Publication Data

US 2020/0030152 A1    Jan. 30, 2020

Related U.S. Application Data

(63) Continuation of application No. 15/813,615, filed on Nov. 15, 2017, now Pat. No. 10,470,936, which is a continuation-in-part of application No. 15/680,524, filed on Aug. 18, 2017, now Pat. No. 10,434,015, which is a continuation of application No. 13/778,538, filed on Feb. 27, 2013, now Pat. No. 9,763,833.

(60) Provisional application No. 61/668,178, filed on Jul. 5, 2012, provisional application No. 61/604,663, filed on Feb. 29, 2012.

(51) Int. Cl.
| | |
|---|---|
| A61F 13/02 | (2006.01) |
| C09J 123/20 | (2006.01) |
| A61F 5/443 | (2006.01) |
| A61L 26/00 | (2006.01) |
| A61L 24/04 | (2006.01) |
| A61L 24/00 | (2006.01) |
| C09J 133/02 | (2006.01) |
| C08L 33/02 | (2006.01) |
| A61L 15/60 | (2006.01) |
| A61L 15/58 | (2006.01) |
| C08L 23/18 | (2006.01) |
| C08L 53/02 | (2006.01) |
| C09J 123/22 | (2006.01) |

(52) U.S. Cl.
CPC .......... *A61F 13/0253* (2013.01); *A61F 5/443* (2013.01); *A61F 13/0203* (2013.01); *A61L 15/585* (2013.01); *A61L 15/60* (2013.01); *A61L 24/0031* (2013.01); *A61L 24/043* (2013.01); *A61L 26/008* (2013.01); *A61L 26/0052* (2013.01); *C08L 23/18* (2013.01); *C08L 33/02* (2013.01); *C08L 53/02* (2013.01); *C09J 123/20* (2013.01); *C09J 123/22* (2013.01); *C09J 133/02* (2013.01); *C08L 2205/16* (2013.01); *C08L 2205/22* (2013.01)

(58) Field of Classification Search
CPC .. A61F 13/0253; A61F 13/0203; A61F 5/443; A61L 15/585; A61L 24/06; A61L 24/043; A61L 15/58; C08L 23/22; C09J 123/20; C09J 133/02

See application file for complete search history.

(56) References Cited

U.S. PATENT DOCUMENTS

| | | | |
|---|---|---|---|
| 4,538,603 A | 9/1985 | Pawelchak et al. | |
| 4,775,374 A | 10/1988 | Cilento et al. | |
| 4,952,618 A | 8/1990 | Olsen | |
| 5,750,136 A | 5/1998 | Scholz et al. | |
| 7,767,291 B2 | 8/2010 | Taylor | |
| 9,763,833 B2 | 9/2017 | Taylor et al. | |
| 10,470,936 B2* | 11/2019 | Wohlgemuth | ...... A61L 24/0031 |
| 2004/0156886 A1 | 8/2004 | Kose | |
| 2005/0215727 A1 | 9/2005 | Feldstein et al. | |
| 2010/0286640 A1 | 11/2010 | Nordby et al. | |
| 2011/0040270 A1 | 2/2011 | Ciok et al. | |
| 2013/0231600 A1 | 9/2013 | Tyler et al. | |
| 2015/0045711 A1 | 2/2015 | Taylor et al. | |

FOREIGN PATENT DOCUMENTS

| | | |
|---|---|---|
| CN | 1361702 | 7/2002 |
| CN | 104548193 | 4/2015 |
| CN | 106714744 | 5/2017 |

(Continued)

OTHER PUBLICATIONS

Office Action issued in corresponding JP Application No. 2019-168112 dated Oct. 27, 2020.

(Continued)

*Primary Examiner* — Jeffrey C Mullis
(74) *Attorney, Agent, or Firm* — Grogan, Tuccillo & Vanderleeden, LLP (57) ABSTRACT

Provided are buffered adhesive compositions comprising a high molecular weight non-neutralized polymeric acid and a high molecular weight partially neutralized polymeric acid and products such as wound dressings and ostomy skin barriers incorporating the compositions.

12 Claims, 4 Drawing Sheets

(56) References Cited

FOREIGN PATENT DOCUMENTS

| | | |
|---|---|---|
| JP | 2005-131400 | 5/2005 |
| JP | 2009-521964 | 6/2009 |
| JP | 2009-523510 | 6/2009 |
| JP | 2013034868 | 2/2013 |
| JP | 2015-508421 | 3/2015 |
| WO | 2006118173 | 11/2006 |
| WO | 2007092289 | 8/2007 |
| WO | 2010095578 | 8/2010 |
| WO | 2013130566 | 9/2013 |
| WO | 2016028297 | 2/2016 |
| WO | 2016124203 | 8/2016 |

OTHER PUBLICATIONS

Examination Report dated Oct. 9, 2020 Issued in AU Patent Application No. 2018369903.
Office Action dated Jun. 4, 2021 Issued in CN Patent Application No. 201880068961.2.

\* cited by examiner

BUFFERED ADHESIVE COMPOSITIONS FOR SKIN-ADHERING MEDICAL PRODUCTS

CROSS-REFERENCE TO RELATED APPLICATIONS

This application is a continuation application of Ser. No. 15/813,615, filed on Nov. 15, 2017, which is a continuation in part application of Ser. No. 15/680,524, filed on Aug. 18, 2017, which, in turn, is a continuation application of U.S. application Ser. No. 13/778,538, filed Feb. 27, 2013 (now U.S. Pat. No. 9,763,833), which claims priority from U.S. provisional applications 61/604,663, filed Feb. 29, 2012, and 61/668,178, filed Jul. 5, 2012, all of which are incorporated herein by reference in their entirety.

FIELD OF THE DISCLOSURE

This disclosure relates to the technical field of adhesive compositions for medical dressings and skin-adhering devices such as ostomy products, wound dressings, and other medical products intended to be adhesively secured to skin surfaces of users. The disclosure is specifically concerned with such adhesive compositions that contain a high molecular weight buffer and are capable of absorbing fluids and maintaining normal skin pH levels and to methods for making the compositions.

BACKGROUND

In a number of medical uses, a product is adhered directly to the skin, such as in the case of a wound dressing or an ostomy skin barrier. Such a product must be securely affixed to the skin to keep it in place and must absorb whatever fluid is produced under or near it, such as perspiration, wound exudate, fluid fecal matter, and the like.

Wound dressings typically perform several functions to facilitate healing. These functions include absorbing wound exudate, regulating pH to create an optimal healing environment and reduce microbial activity, and protecting the wound from infection. Many such wound dressings are self-adhesive and contain an adhesive layer that typically adheres to the peri-wound skin of a wearer. It is known that skin often becomes irritated under wound dressings.

Known wound dressings achieve the aforementioned functionality through the use of several individual components. For example, known dressings often use hydrocolloids, e.g., carboxymethylcellulose (CMC), pectin, or gelatin, to absorb wound exudate. While some hydrocolloids are also capable of independently adjusting pH, the degree of pH buffering they can provide is limited by the amount of available hydrocolloid in the dressing, which, in turn, is dependent: on the desired fluid handling properties of the dressing. Moreover, the buffering effect of hydrocolloids alone is not optimal.

Additionally, appropriate levels of both absorption and pH control are often difficult to achieve simultaneously. A certain extent of absorption by the wound dressing is required for pH control and is generally desirable in a wound dressing. However, the absorption of an excessive amount of fluid can cause an undesirable amount of swelling of the wound dressing, leading to distension and possible loss of adhesion. In certain instances, absorption of an excessive amount of fluid can cause dissolution of the adhesive composition, which is also highly undesirable.

Adhesive compositions containing hydrocolloids are well known, as disclosed, for example, in U.S. Pat. Nos. 5,571,080, 3,339,546, 4,192,785, 4,296,745, 4,367,732, 4,813,942, 4,231,369, 4,551,490, 4,296,745, 4,793,337, 4,738,257, 4,867,748, 5,059,169, and 7,767,291, the disclosures of which are incorporated herein by reference. Hydrocolloids are commonly used in what is commonly referred to as hydrocolloid skin barriers or hydrocolloid wound dressings. Such skin barriers and wound dressings normally include a water-insoluble pressure-sensitive adhesive as a continuous phase with particles of one or more hydrocolloids dispersed throughout the adhesive as a liquid-absorbing and swellable discontinuous phase.

The water-insoluble adhesive phase of commercial skin barriers and wound dressings typically consists of polyisobutylene (PIB), or block copolymers such as styrene-isoprene-styrene (SIS), or blends of these materials. The surface tack may be modified by the addition of tackifier components.

Patients with a permanent or temporary ostomy (colostomy, ileostomy, and the like) have need of a pouch to contain the expelled fecal material or urine. The pouch is normally attached to the peristomal skin with an adhesive skin barrier that attaches the pouch to the skin and absorb liquids flowing from the stoma or produced by the peristomal skin. A skin barrier is normally replaced every three to five days but may remain in place for up to a week. During use of the barrier, the peristomal skin may become irritated due to prolonged contact with the fecal material. Over time, the irritation can become severe.

In some applications, an ostomy skin barrier has an adhesive tape border around its periphery for additional security. The adhesive for said border is typically an acrylic adhesive. As used herein, the term "skin barrier" is intended to include any skin barrier either with or without an adhesive tape border.

Both wound exudate and fecal material contain proteolytic and lipolytic enzymes. These enzymes, when contained in a closed, moist environment, are thought to degrade the stratum corneum and contribute to the observed irritation. Moreover, since both wound dressings and ostomy skin barriers are normally removed and reapplied on a regular basis, the integrity of the skin under them becomes compromised and more susceptible to irritation than normal skin.

Normal skin has a so-called "acid mantle" which maintains the surface of the skin at a pH typically between about 4.0 and 5.5 (slightly acidic). This pH range promotes the growth of beneficial microorganisms and retards the growth of harmful microorganisms, while helping to maintain the integrity of the skin. At this pH level, the activity of (and hence the damage caused by) the proteolytic and lipolytic enzymes from wound exudate or fecal matter would not be severe. However, the wound exudate and stomal fluid normally have a pH in the range of 6.0 to 8.0. This increase in pH over the normal skin pH causes a significant increase in the activity of the enzymes and hence in their ability to cause irritation.

As for wound dressings, appropriate levels of both absorption and pH control are often difficult to achieve simultaneously for ostomy skin barriers. A certain extent of absorption by the skin barrier is required for pH control and is generally desirable. However, the absorption of an excessive amount of fluid can cause an undesirable amount of swelling of the skin barrier, leading to distension and possible loss of adhesion. In certain instances, absorption of an excessive amount of fluid can cause dissolution of the adhesive composition, which is also highly undesirable.

Current skin barriers incorporating hydrocolloids such as pectin and CMC have only limited pH buffering capacity. When exposed to water or saline solution, they are capable of adjusting pH to a level in the desired range from about 4.0 to 5.5. However, it is important to note that physiological fluids such as stoma output or wound exudates are also buffered, typically at pH levels close to neutral. When current skin barriers are exposed to such fluids, the strong buffering capacity inherent in the physiological fluid overwhelms the weak buffering capacity of the skin barrier. As a result, the pH at the surface of the skin barrier increases to approach the pH of the fluid used to challenge the skin barrier. Thus, it would be desirable to provide a skin barrier with enhanced pH buffering capacity. It would also be desirable to provide a skin barrier with optimal absorption characteristics.

In view of the above, it would be desirable to have an adhesive composition containing a suitable buffer to maintain the pH of the skin under a wound dressing or a stomal skin barrier or the like product at about 4.0 to about 5.5 without being inherently irritating to the user's skin, and which would have an optimal extent of fluid absorption.

SUMMARY

In accordance with one aspect of the disclosure, a high molecular weight polymeric buffering adhesive composition is provided that is capable of optimal fluid absorption and pH buffering.

In accordance with another aspect of the disclosure, a wound dressing is provided that includes a high molecular weight polymeric buffer composition capable of optimal fluid absorption and pH buffering.

In accordance with another aspect of the disclosure, an ostomy skin barrier is provided that includes a high molecular weight polymeric buffer composition capable of optimal fluid absorption and pH buffering.

In accordance with another aspect of the disclosure, a method is provided for using the high molecular weight polymeric buffer composition to manufacture a skin-adhering medical device, such as a wound dressing or ostomy skin barrier.

An embodiment of the disclosure is a wound dressing that includes a flexible outer layer and a high molecular weight polymeric buffering adhesive composition applied to one side thereof, said adhesive providing pH buffering and optimal fluid absorption with minimal irritation to a wearer's skin.

Another embodiment of the disclosure is an ostomy skin barrier that includes a high molecular weight polymeric buffering adhesive composition applied to one side thereof, said adhesive composition providing pH buffering and optimal fluid absorption with minimal irritation to a wearer's skin.

BRIEF DESCRIPTION OF THE DRAWINGS

The present invention will be better understood from reading the following description of non-limiting embodiments, with reference to the attached drawings, wherein below.

DESCRIPTION OF PREFERRED EMBODIMENTS

One embodiment of the present disclosure is directed to an adhesive composition comprising a high molecular weight buffer that absorbs fluids such as perspiration, wound exudate, urine and fecal matter, adjusts pH, and reduces enzymatic activity. As will be appreciated, embodiments of the adhesive composition are suitable for use in medical applications such as wound care, e.g., wound dressings, ostomy barriers and the like, and may be suitable for use in both human and veterinary applications.

In particular, an embodiment of the present disclosure contemplates use of high molecular weight polymers that are rich in acidic sites. Polymers with polyacid functionality can serve as buffers through the use of mixtures of their protonated and neutralized forms. Any high molecular weight polymer having pendant carboxyl groups that are capable of being partially neutralized is suitable for use in the present disclosure. Suitable polymers include, for example, polyacrylic acid and poly(2-alkyl acrylic acid) in which the alkyl chain is from one to five carbons in length and may be straight chain or branched chain. Poly methacrylic acid is the preferred poly (2-alkyl acrylic acid). Other suitable polymers are copolymers of any of acrylic acid and 2-alkyl acrylic acid monomers, copolymers of the foregoing monomers with maleic acid, olefinic polymers substituted with side chains containing free carboxylic acid groups, such as polyvinyl alcohol esterified with a diacid, triacid or polyacid (e.g., polyvinyl alcohol succinate), and the like.

As will be appreciated by one of skill in the relevant art, the buffering adhesive composition of the disclosure can employ any high molecular weight polymer having partially neutralizable pendant carboxyl groups that is capable of maintaining the pH of a test product at less than about 6.0 in the phosphate buffer challenge test described in Example 1.

A preferred embodiment of the present invention is a buffering adhesive composition that comprises at least two high molecular weight polymers that are rich in acidic sites, one of which is in its non-neutralized form and the other of which is partially neutralized. The inventors have surprisingly discovered that the combination of non-neutralized and partially neutralized forms of a high molecular weight polymer rich in acidic sites permits independent modification of the extent of absorption and of pH control, a highly desirable quality in an adhesive composition for a medical device to be attached to a patient's skin, such as a wound dressing or an ostomy skin barrier.

The proportion of non-neutralized and partially neutralized polyacids, and the extent of neutralization of the partially neutralized polyacid are interrelated. The extent of neutralization of the partially neutralized polyacid may conveniently be from about 50% to about 100%, about 75% being preferred. Whatever extent of neutralization is selected, the proportion of non-neutralized and partially neutralized polyacid should be adjusted to achieve the desired pH range of between 4.0 and about 5.5 under the wound dressing or ostomy skin barrier. Those of ordinary skill in the adhesive formulation art can readily select an appropriate proportion of non-neutralized polyacid and partially neutralized polyacid for a given extent of neutralization of the partially neutralized polyacid.

In this preferred embodiment, and for a partially neutralized cross linked polyacid that is about 75% neutralized, the non-neutralized form and the partially neutralized form of the high molecular weight polymeric acids may be present in a ratio of from about 3:1 to about 1:4 and preferably from about 2:1 to about 1:1. The two forms of the high molecular weight polymeric acids together may comprise from about 10 wt. % to about 25 wt. % of the entire adhesive composition, and preferably from about 15% to about 20% of the entire adhesive composition.

Polymers particularly well suited for use in an embodiment of the disclosure include polyacrylic acid (PAA) and polymethacrylic acid (PMA). Both PAA and PMA are available from, for example, Sigma-Aldrich Co., in a variety of forms, e.g., powder and solution, and in a range of molecular weights. Of the acrylic acid derivatives, PAA is preferred because it has the highest density of carboxylic acid sites per gram of compound and hence the highest extent of buffering per gram of compound. As used herein, "high molecular weight" PAA means greater than about 60,000 Daltons and as high as several million Daltons. The term has similar meanings for PMA and the other polymers described above.

One of ordinary skill in the art can readily determine the appropriate degree of neutralization for a particular polymer and use. Partial neutralization of PAA may be achieved by mixing PAA (plus water if appropriate) with a stoichiometrically appropriate amount of a strong base (e.g., NaOH) until the desired degree of neutralization is achieved. Other polymers may be treated similarly. Partially neutralized polyacids such as PAA are also available commercially.

PAA and related polymers exist in both cross linked and non-cross linked forms and the degree of cross-linking can be varied. The polymers used in the present disclosure are preferably cross linked.

As stated, high molecular weight polymers, e.g., PAA and PMA, provide both effective pH buffering and absorb fluids such as perspiration, wound exudate, or fecal matter. More specifically, the polymers function similarly to hydrocolloids such as pectin and CMC when dispersed within an adhesive matrix. That is, they absorb and swell and form viscous solutions that provide mucoadhesion against a wearer's skin. As will be appreciated, the high molecular weight polymers may be the sole hydrocolloid component or in other embodiments, they may be combined with other hydrocolloids, depending on the application and desired fluid handling capabilities of the wound dressing or skin barrier.

In one embodiment of the disclosure, high molecular weight cross linked PAA and high molecular weight cross linked partially neutralized PAA are combined with polyisobutylene and either styrene-isoprene-styrene copolymer or polymer fibers (or both). In one such embodiment, the adhesive composition comprises cross linked high molecular weight PAA, cross linked high molecular weight partially neutralized PAA, polyisobutylene, and styrene-isoprene-styrene block copolymer. In another such embodiment, the adhesive composition comprises cross linked high molecular weight PAA, cross linked high molecular weight partially neutralized PAA, polyisobutylene, styrene-isoprene-styrene block copolymer and fibers such as cotton or preferably polyolefin such as polyethylene or polypropylene.

The adhesive component of the compositions of this disclosure may be any material that has pressure-sensitive adhesive properties with a strong affinity for the material of the fibers (if fibers are used). It may be a single pressure-sensitive adhesive or a combination of two or more pressure-sensitive adhesives. Adhesives useful in the present disclosure include, for example, those based on natural rubbers, synthetic rubbers, styrene block copolymers, polyvinyl ethers, poly(meth) acrylates (including both acrylates and methacrylates), polyolefins and silicones. A particular adhesive believed to be a preferred material of choice for this disclosure is a polyolefin, namely, polyisobutylene (PIB), but other pressure-sensitive adhesive materials having similar properties are believed suitable.

The fibers in the adhesive composition may be any fibrous material known in the art but preferably are compatible with, and even have a strong affinity for, the tacky adhesive component. It has been found that polyolefins such as polyethylene and polypropylene are highly compatible with PIB and are easily wetted by that adhesive medium. Both are non-polar saturated hydrocarbons.

Preferably such PIB is present as relatively high molecular weight PIB (molecular weight in the range of about 40,000 to 60,000). For example, a skin barrier for ostomy use would normally contain 60,000 molecular weight PIB in the range of 50 wt. % to 65 wt. % or 40,000 molecular weight PIB in the range of 40 wt. % to about 55 wt. %. Additionally, combinations of 40,000 molecular weight and 60,000 molecular weight PIB may also be used, such as 32.5 wt. % 40,000 molecular weight PIB and 32.5 wt. % 60,000 molecular weight PIB.

Whatever materials are chosen for the buffering adhesive composition of the disclosure, it is highly desirable that the composition be at least minimally absorptive. The buffering capability of the present compositions is related in part to their absorptive capability. If no absorption were to occur, the high molecular weight polymeric buffer would not be contacted by the wound exudate or fecal material and hence would not be effective. Although compositions having lower absorptive capacity are included within the present disclosure, the compositions of the disclosure should preferable have an absorptive capacity of at least about 0.15 g/cm$^2$ as measured in the test of Example 1. Additionally, the absorptive capacity of the buffering adhesive composition should preferably not exceed 0.60 g/cm$^2$. Since, as can be seen below, the absorptive capacity of the buffering adhesive composition can be adjusted by varying the proportion of the partially neutralized high molecular weight polymer relative to the non-neutralized high molecular weight polymer, one of skill in the art can readily adjust the absorptive capacity of the buffering adhesive composition to the desired level.

Preferred representative buffered adhesive compositions of the invention include the following: 1) about 55.5 wt. % PIB, about 14.5 wt. % SIS, about 5% polyethylene fibers, about 15 wt. % cross linked polyacrylic acid, and about 10 wt. % partially neutralized cross linked polyacrylic acid; and 2) about 66 wt. % PIB, about 6.5 wt. % SIS, about 4% polyethylene fibers, about 14.5 wt. % cross linked polyacrylic acid, and about 9 wt. % partially neutralized cross linked polyacrylic acid. In the above compositions, the PIB preferably has a viscosity average molecular weight of 40,000 and the partially neutralized cross linked polyacrylic acid is preferably 75% neutralized.

The following Examples describe the manufacture and testing of representative embodiments of the disclosure.

Example 1

Test Samples: Test samples were prepared by heat compression of barrier materials to a thickness of 0.020 inches and were laminated between a removable release liner and a flexible backing film.

Materials

Polyisobutylene (PIB)

Nippon Himol 4H with viscosity average molecular weight 40,000 produced by JX Nippon Oil and Energy Styrene-Isoprene-Styrene Block Copolymer (SIS)

Kraton™ D-1161P produced by Kraton Polymers

Polyolefin Fibers

Polyethylene Short Stuff Synthetic Pulp E380F supplied by MiniFIBERS, Inc.

Cross Linked Polyacrylic Acid

Carbopol® 980 NF provided by The Lubrizol Corporation.

Cross Linked Partially Neutralized Polyacrylic Acid

Aqua Keep™ 10 SH-PF provided by Sanyo Corporation of America.

Fluid Absorption and pH: Fluid absorption was measured following the practice of standard EN 13726-1:2002 (Test methods for primary wound dressings—Part 1: Aspects of absorbency, Section 3.3). The hydrating fluid was normal saline (0.9% NaCl in water). The mass of fluid absorbed was measured by the weight gain in samples of 10 cm$^2$ surface area exposed to 20 mL normal saline. Samples were maintained in an oven (37° C., 15% relative humidity) for fixed time periods. Surface pH measurements were performed on samples following fluid absorption using a calibrated pH meter and a flat pH probe (Ross® model 8135BN).

pH Buffer Challenge: A stock buffer solution (100 mM in Phosphate, 0.9% NaCl, pH 7.4) was prepared. Lower phosphate concentration buffers were prepared by dilution of the stock buffer with appropriate volumes of 0.9% NaCl. A 10 cm$^2$ surface of the barrier was exposed to 10 mL of buffer challenge solution.

Example Formulations

A series of formulations based on PIB, polyethylene fibers and partially neutralized polyacrylic acid (with two different molecular weights and two different degrees of neutralization) were prepared.

Compositions were prepared using a Brabender Type REE6 mixer at 85° C. A 'masterbatch' containing 85% SIS and 15% PIB was prepared separately. The required weight of masterbatch was added to the mixer and was mixed at 36 rpm for 4 minutes. One-half the required amount of PIB was added and mixing was continued for 4 minutes. The required amounts of dry powders (PE fibers, Carbopol 980 NF and Aqua Keep 10SH-PF) were pre-blended and then added to the mixer over a 4 minute period. The remaining one-half of the PIB ingredient was added and the mixing was continued for 10 minutes. The mixing chamber was sealed and vacuum was applied and mixing was continued for 15 minutes. Vacuum was released and the mixtures were removed from the mixer and allowed to equilibrate at room conditions before any testing was undertaken. Tests were performed as in Example 1. Table 1 below shows compositions prepared in this fashion with weight percentages of the indicated ingredients along with testing results for these compositions.

TABLE 1

| Nippon 4H PIB | Styrene-Isoprene-Styrene Copolymer | PE fibers | Carbopol 980 NF | Aqua Keep 10 SH-PF | 6 Hour Fluid Absorption | 6 Hour Surface pH | 24 Hour Surface pH | 24 Hour Fluid Absorption | 24 Hour Buffer Challenge Surface pH |
|---|---|---|---|---|---|---|---|---|---|
| 64.6% | 10.4% | 4.0% | 16.0% | 5.0% | 0.138 | 3.96 | 3.98 | 0.166 | 5.68 |
| 62.4% | 14.9% | 5.8% | 8.0% | 9.0% | 0.197 | 4.82 | 4.72 | 0.266 | 6.2 |
| 55.7% | 25.0% | 4.0% | 11.3% | 4.0% | 0.078 | 4.54 | 4.44 | 0.135 | 6.31 |
| 50.9% | 10.0% | 8.0% | 15.1% | 16.0% | 0.333 | 4.70 | 4.66 | 0.590 | 5.67 |
| 74.2% | 10.0% | 5.8% | 6.0% | 4.0% | 0.083 | 4.74 | 4.76 | 0.098 | 6.71 |
| 64.3% | 10.0% | 5.7% | 4.0% | 16.0% | 0.365 | 5.42 | 5.36 | 0.602 | 6.54 |
| 73.0% | 10.0% | 4.0% | 4.0% | 9.0% | 0.202 | 5.20 | 5.13 | 0.248 | 6.72 |
| 50.0% | 14.0% | 4.0% | 16.0% | 16.0% | 0.298 | 4.69 | 4.55 | 0.391 | 5.62 |
| 73.9% | 10.0% | 7.8% | 4.3% | 4.0% | 0.050 | 5.31 | 5.43 | 0.051 | 7.26 |
| 58.5% | 16.6% | 5.9% | 9.4% | 9.4% | 0.188 | 4.80 | 4.75 | 0.205 | 6.35 |
| 63.0% | 25.0% | 4.0% | 4.0% | 4.0% | 0.041 | 5.65 | 5.67 | 0.045 | 7.31 |
| 50.0% | 22.4% | 4.0% | 7.6% | 16.0% | 0.286 | 5.35 | 5.27 | 0.422 | 6.46 |
| 59.4% | 10.0% | 4.0% | 16.0% | 10.6% | 0.227 | 4.44 | 4.31 | 0.276 | 5.63 |
| 50.0% | 18.7% | 8.0% | 16.0% | 7.3% | 0.160 | 4.29 | 4.14 | 0.182 | 5.67 |
| 74.0% | 10.0% | 8.0% | 4.0% | 4.0% | 0.045 | 5.34 | 5.35 | 0.067 | 7.26 |
| 51.9% | 24.6% | 4.4% | 15.1% | 4.0% | 0.086 | 4.20 | 4.16 | 0.105 | 5.77 |
| 54.0% | 25.0% | 6.1% | 5.7% | 9.2% | 0.140 | 5.75 | 5.71 | 0.174 | 7.06 |
| 61.9% | 16.7% | 8.0% | 4.0% | 9.5% | 0.147 | 5.73 | 5.70 | 0.254 | 7.08 |
| 63.4% | 10.0% | 8.0% | 4.0% | 14.6% | 0.250 | 5.43 | 5.36 | 0.600 | 6.6 |
| 61.7% | 16.7% | 5.9% | 11.8% | 4.0% | 0.089 | 4.28 | 4.26 | 0.107 | 6.08 |
| 73.8% | 10.1% | 4.0% | 8.1% | 4.0% | 0.048 | 5.62 | 5.53 | 0.088 | 7.3 |
| 59.0% | 25.0% | 4.0% | 6.0% | 6.0% | 0.105 | 5.28 | 5.29 | 0.133 | 7.23 |
| 62.5% | 21.2% | 8.0% | 4.4% | 4.0% | 0.032 | 5.72 | 5.61 | 0.035 | 7.41 |
| 54.1% | 25.0% | 8.0% | 8.9% | 4.0% | 0.073 | 4.78 | 4.99 | 0.073 | 7.31 |
| 64.7% | 10.0% | 8.0% | 13.3% | 4.0% | 0.115 | 3.95 | 3.91 | 0.124 | 5.89 |
| 60.2% | 10.0% | 6.2% | 7.6% | 16.0% | 0.372 | 5.15 | 5.01 | 0.598 | 6.29 |
| 54.7% | 10.0% | 8.0% | 11.3% | 16.0% | 0.356 | 4.89 | 4.83 | 0.473 | 5.99 |
| 50.0% | 23.8% | 4.0% | 11.6% | 10.5% | 0.254 | 4.77 | 4.65 | 0.295 | 6.1 |
| 50.0% | 25.0% | 8.0% | 4.0% | 13.0% | 0.336 | 5.88 | 5.89 | 0.601 | 6.85 |

TABLE 1-continued

| Nippon 4H PIB | Styrene-Isoprene-Styrene Copolymer | PE fibers | Carbopol 980 NF | Aqua Keep 10 SH-PF | 6 Hour Fluid Absorption | 6 Hour Surface pH | 24 Hour Surface pH | 24 Hour Fluid Absorption | 24 Hour Buffer Challenge Surface pH |
|---|---|---|---|---|---|---|---|---|---|
| 62.2% | 13.8% | 4.0% | 4.0% | 16.0% | 0.543 | 5.53 | 5.60 | 0.705 | 6.57 |
| 50.5% | 25.0% | 4.5% | 4.0% | 16.0% | 0.549 | 5.78 | 5.88 | 0.508 | 6.75 |
| 58.5% | 16.6% | 5.9% | 9.4% | 9.4% | 0.231 | 4.77 | 4.77 | 0.308 | 6.32 |

In order to meet user needs, it is necessary to adjust the fluid absorption and pH control properties of the skin barriers. In the current formulations, the ingredient levels of the two polyacrylate components, the non-neutralized cross linked high molecular weight polyacrylic acid Carbopol 980 NF and the partially neutralized cross linked high molecular weight polyacrylic acid Aqua Keep 10 SH-PF are primarily responsible for the fluid absorption and pH properties. The ability to independently adjust absorption and pH properties would be advantageous since it would enable formulation of a range of barriers with different sets of properties. While acknowledging that the overall properties of the barriers are influenced by the relative amounts of all the ingredients, it has been surprisingly found that the partially neutralized cross linked high molecular weight polyacrylic acid component has the major influence on absorption and minimal influence on the pH properties while the non-neutralized cross linked high molecular weight polyacrylic acid component has the major influence on the pH properties and minimal influence on the absorption properties. These effects are shown by examining the correlations between product performance properties and ingredient levels for these two components. This is illustrated graphically by plotting the 24 hour fluid absorption results against ingredient levels for the two ingredients.

Figure 1:
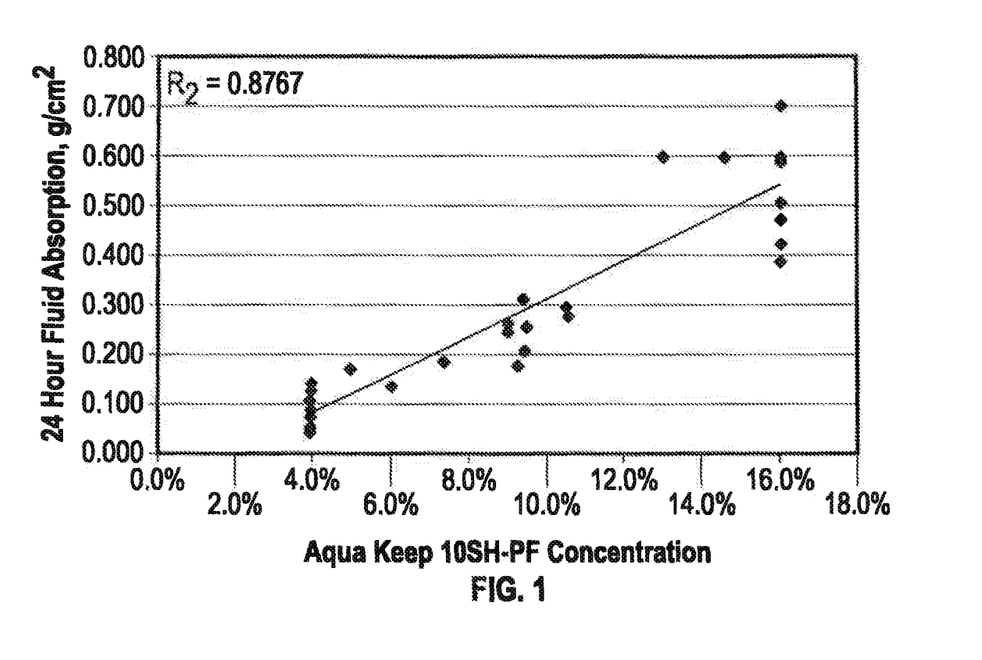
FIG. 1 illustrates a dependence of absorption on Aqua Keep concentration for a set of barriers according to embodiments of the invention.
Figure 2:
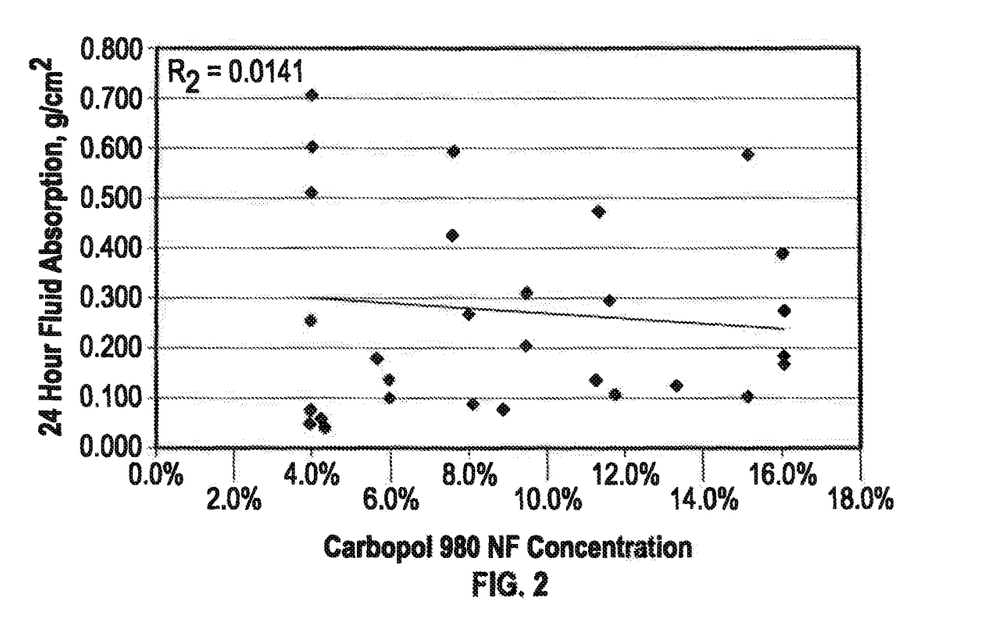
FIG. 2 illustrates fluid absorption relative to Carbopol concentration according to an embodiment of the invention.

FIG. 1 illustrates the dependence of absorption on the Aqua Keep concentration for the full set of barriers. The straight line is the linear regression fit to the data. The $R^2$ value of 0.8757 means that more than 87% of the observed variation in measured fluid absorption is correlated with the variation in the Aqua Keep concentration. In contrast, there is essentially no correlation between fluid absorption and Carbopol concentration ($R^2=0.0141$) as illustrated in FIG. 2.

Figure 3:
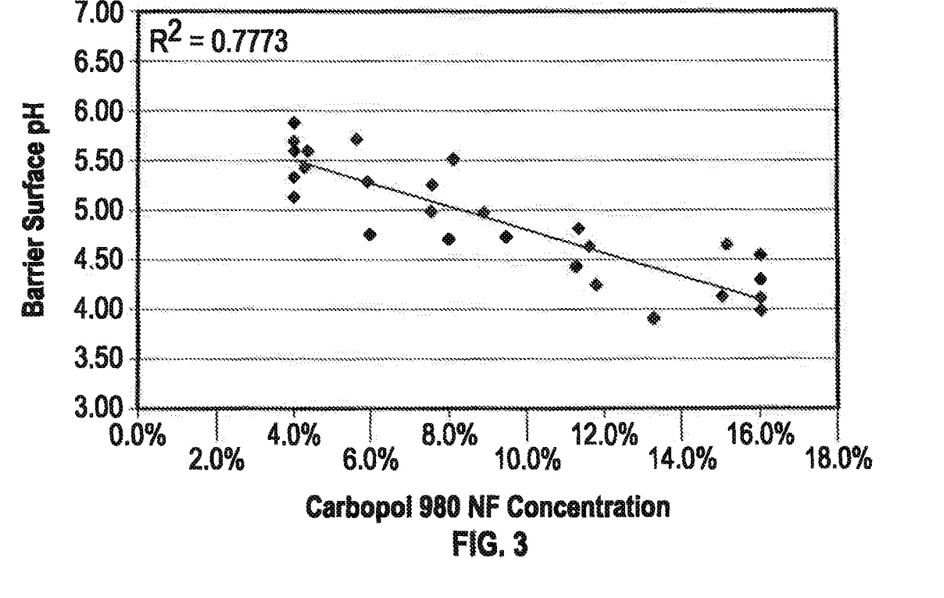
FIG. 3 illustrates a correlation between pH of a barrier surface relative to Carbopol concentration according to an embodiment of the invention.
Figure 4:
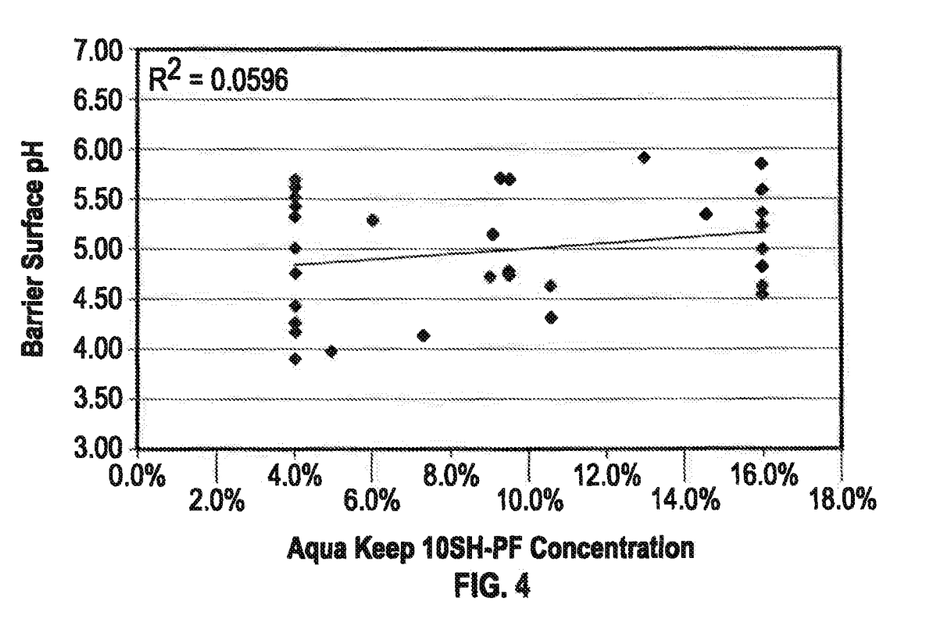
FIG. 4 illustrates a correlation between pH of a barrier surface relative to Aqua Keep concentration according to an embodiment of the invention.

In a similar fashion, FIGS. 3 and 4 illustrate that the pH of the barrier surface is strongly correlated with Carbopol 980 NF concentration (FIG. 3, $R^2=0.7773$) while there is essentially no correlation with Aqua Keep 10SH-PF concentration (FIG. 4, $R^2=0.0596$).

High molecular weight polymers such as those set forth above provide both enhanced pH buffering capacity and absorption with reduced skin irritation. The inventors have surprisingly discovered that low molecular weight acids, such as citric acid, are unsuitable for buffer systems in the present disclosure. Although such low molecular weight acids function acceptably as buffers, low molecular weight acid buffer systems cause unacceptable irritation to the user's skin for use as contemplated herein. When a buffering adhesive compositions similar to those of the disclosure but using a citric acid/citrate buffer instead of a high molecular weight polymer buffer was used in an adhesive dressing on human subjects, the subjects developed punctate ulcers under the dressing. The test results are shown below. Such an adhesive composition would be unsuitable for medical use. This result was both surprising and unexpected. The evaluation of a citric acid buffering system is described in Example 2 below.

Example 2

In 1968, Lanman et al., reported that several days of repeated exposures produced a method to discriminate among mildly irritating cosmetic type products. With modification including shorter time periods (e.g., 21 days) this method has remained the standard test for determining a product's potential for mild cutaneous irritation. The methodology involves 21 consecutive daily applications under occlusion. A 1% sodium lauryl sulfate (SLS) solution applied on a non-woven pad served as the positive control while preservative-free 0.9% sodium chloride applied in a similar manner served as the negative control. This standard test was used to assess the irritation potential of various barrier formulations applied directly to skin for 21 consecutive applications. Because the barrier materials are self-adhesive, it was possible to partially differentiate between the contribution from irritation due to mechanical properties (skin stripping) and chemical irritation, by comparing irritation resulting from direct application with that observed when the barrier was isolated from the skin using a non-woven pad moistened with sterile normal saline as well as using barriers constructed with and without buffering material.

A sufficient number of normal volunteer subjects was recruited to ensure completion with 30. Each subject was exposed to all test materials and the sites were randomized using a standard Latin Square design. Graders were blinded to the identity of the materials. Materials were reapplied to the same site for 21 consecutive days or until a discontinuation score was reached. The irritation data was treated using rank sum analysis. Rank sums range from 1 to 10 with higher numbers indicating more irritation.

Formulations used in the irritation test are described below:

Citrate Barrier

| | |
|---|---|
| Oppanol ® B12 PIB (BASF) | 44.0% |
| TPC Group TPC1285 liquid PIB | 7.0% |
| Polyethylene Fiber | 3.5% |
| Pectin | 8.5% |
| Sodium Carboxymethyl Cellulose | 17.0% |
| Monosodium citrate Anhydrous | 16.0% |
| Trisodium Citrate Dihydrate | 4.0% |

PAA Barrier

| | |
|---|---|
| Oppanol ® B12 PIB (BASF) | 55.0% |
| TPC Group TPC1285 liquid PIB | 8.7% |
| Polyethylene Fiber | 4.4% |
| Partially neutralized PAA | 31.9% |

Using this standard methodology, the irritation potential of the formulation containing 20% citrate barrier (mean rank 9.59) was similar to that of the positive control (mean rank 9.27). Only the barrier formulation containing citrate caused irritation accompanied by focal erosions (punctate lesions), which was different from the more uniform irritation typically observed with exposure to SLS. The barrier formulated with PAA (mean rank 6.70) was significantly less irritating that either the positive control or the citrate buffer formulation. The slight irritation observed due to repeated exposure to the PAA barrier formulation was more uniform 'glazing' characteristic of repeated mechanical trauma, i.e., tape stripping. Both of these groups were different from the negative control (mean rank 2.68). The PAA buffer applied in petrolatum (31.8% PAA in petrolatum) was non-irritating, indicating a lack of inherent chemical irritation due to repeated exposure to PAA. This observation is consistent with the interpretation that the minor irritation observed with the barrier formulated with PAA is due to repeated mechanical damage.

An embodiment of the present disclosure contemplates the use of a high molecular weight polymeric buffer composition incorporated into the adhesive layer of a wound dressing. The wound dressing preferably includes a flexible outer layer such as a film. A hydrocolloid layer is on an inner side of the outer layer and contains the inventive high molecular weight polymeric buffer composition along with, optionally, an additional hydrocolloid such as CMC or pectin. As will be appreciated, the hydrocolloid layer is in direct contact with the wound bed.

In an embodiment, the wound dressing includes an adhesive component having a very high cohesive strength when hydrated to avoid potential disintegration of the dressing components in the wound bed. As will be appreciated, non-adhesive wound dressings incorporating the inventive buffer composition may also be possible.

A formulation suitable for a self-adhesive wound dressing would be, for example, formulation 8 in Table 1 which has high cohesive strength due to the relatively high SIS content along with high fluid absorption and buffering properties, useful for managing wound exudate. Those of ordinary skill in the art would know how to use this formulation in the preparation of a self-adhesive wound dressing.

Another embodiment of the present disclosure contemplates the use of a high molecular weight buffer composition incorporated into an ostomy skin barrier. The skin barrier may be permanently attached to an ostomy pouch (a "one step" or one piece arrangement) or may be separately attached using a flange clip system (a two piece arrangement). This embodiment of the disclosure will maintain the pH of the peristomal skin closer to the normal skin pH range of about 4.0 to about 5.5, thus reducing or eliminating the occurrence of irritation in the peristomal area.

Useful example formulations for ostomy skin barriers include those containing either polyethylene fibers or SIS. For example, formulation 13 of Table 1 combines desirable fluid handling ability with excellent pH control. Those of ordinary skill in the art would know how to use this formulation in the preparation of an ostomy skin barrier.

Also included in the present disclosure are methods of using the above-described high molecular weight polymeric buffer compositions. The compositions may be used to manufacture any skin-adhering device by applying to a side or surface of the device an amount of the composition effective to securely attach the device to the skin of the intended user.

Another embodiment of the present invention contemplates a wound dressing, ostomy barrier, or the like, that includes two or more adhesive compositions. More specifically, a first adhesive containing a high molecular weight polymeric buffer composition, e.g., a composition containing a high molecular weight polymeric acid in non-neutralized form and a high molecular weight polymeric acid in partially neutralized form, such as those set forth Table 1 above and disclosed herein, is paired with a second adhesive that does not include such high molecular weight polymeric buffers. That said, in certain embodiments, the second adhesive may also include a high molecular weight polymeric buffer, or may be another type of adhesive suitable for a particular medical application, e.g., colostomy, ileostomy, urostomy, wound care and the like.

In certain embodiments, the non-neutralized high molecular weight polymeric acid and the partially neutralized high molecular weight polymeric acid of the first adhesive may each be independently selected from the group consisting of polyacrylic acid, poly(2-alkyl acrylic acid), copolymers of acrylic acid and 2-alkyl acrylic acid monomers, copolymers of acrylic acid and 2-alkyl acrylic acid monomers with maleic acid, and olefinic polymers substituted with side chains containing free carboxylic acid groups, wherein alkyl is from one to five carbons in length and may be straight chain or branched chain.

The second adhesive may include natural rubbers, synthetic rubbers, styrene block copolymers, polyvinyl ethers, poly(meth) acrylates (including both acrylates and methacrylates), polyolefins (PIB) and silicones, or other pressure-sensitive adhesive materials. As mentioned, in embodiments, the second adhesive does not utilize high molecular weight polymeric acids for exudate absorption and pH regulation, but includes hydrocolloids to absorb wound exudate and/or regulate pH, Hydrocolloids may include cellulose, pectin, gelatin, alginates, starch, glycogen, chitosan, chitin and derivatives thereof, gum arabic, locust bean gum, karaya gum, ghatti gum, agar-agar, carrageenans, carob gum, guar gum, and xathan gum. In certain embodiments, the second adhesive may utilize low molecular weight acids for pH buffering and may also include polymeric fibers.

The first and second adhesives may be selected based on desired absorption and/or pH buffering capacities. That is, the adhesives may be selected based on the amount of exudate, perspiration, urine or fecal matter that they would potentially encounter in use. For example, the first adhesive, containing a high molecular weight polymeric buffer composition, could be utilized for dermal surfaces in close proximity to a stoma or wound. The second adhesive, e.g., a hydrocolloid based adhesive, could be selected for deployment in areas that do not require a relatively high absorption capacity, or where significant absorption is undesirable, such as the perimeter of a barrier or dressing that might be exposed to water via bathing/showering.

In a particular embodiment, a first adhesive includes 40 wt. % of polyisobutylene (PIB Nippon 4H), 16 wt. % of styrene-isoprene-styrene copolymer (Kraton SIS), 5 wt. % of liquid PIB, 4 wt. % of polyethelyene fibers, 20 wt. % of cross linked polyacrylic acid (Carbopol 980 NF), and 15 wt. % of cross linked partially neutralized polyacrylic acid (Aqua Keep 10SH-PF). A second adhesive, includes 55.5 wt. % polyisobutylene (PIB Nippon 4H), 14.5 wt. % of styrene-isoprene-styrene copolymer (Kraton SIS), 5 wt. % of polyethylene fibers, 8.3 wt. % of pectin, and 16.7 wt. % of carboxymethyl cellulose (CMC)

The first and second adhesives may be incorporated into, placed on, or form different surfaces or portions of a wound dressing or ostomy barrier, i.e., a first barrier surface and a second barrier surface. For example, the adhesive containing the high molecular weight polymeric buffer composition may be located on a barrier surface where significant absorption and/or pH buffering is required. The second adhesive may in turn, be located on a barrier surface where it is in contact with a dermal area that requires less absorption and pH buffering.

Figure 5:
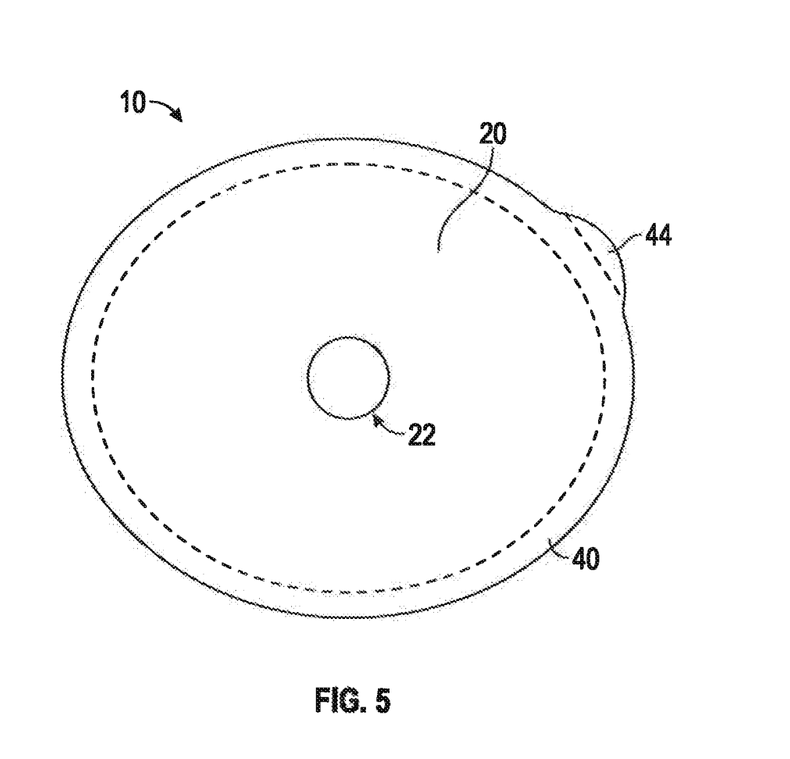
FIG. 5 illustrates an ostomy barrier that includes multiple adhesive components according to an embodiment of the present invention.
Figure 6:
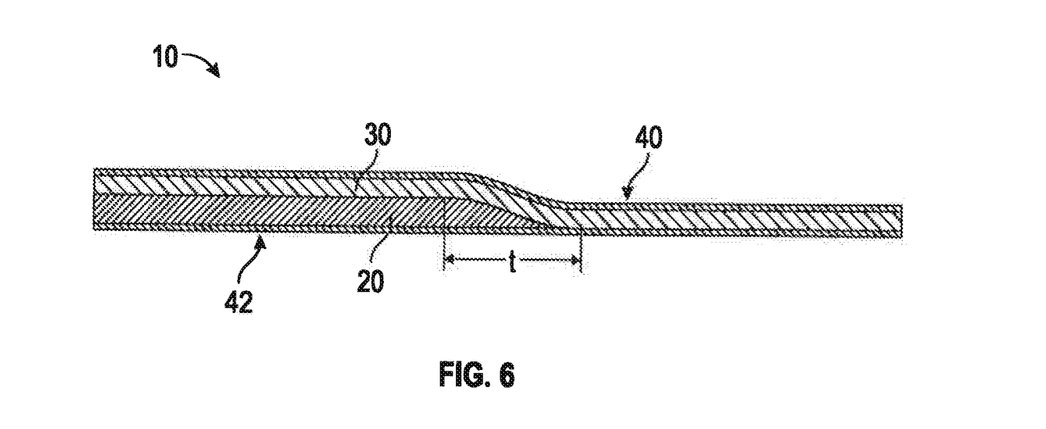
FIG. 6 illustrates a partial cross-sectioned view of the ostomy barrier of FIG. 5.

Referring now to FIGS. 5-6, a particular embodiment of the present disclosure contemplates the use of a first adhesive (containing a high molecular weight buffer composition) and a second adhesive having a different composition from the first, that are both incorporated into an elliptical ostomy barrier 10. As will be appreciated, the barrier 10 may be permanently attached to an ostomy pouch (not shown) or may be attached using a flange clip system.

More specifically, the barrier 10 contains an inner layer 20, which includes the first adhesive, and a backing layer 30, which covers and extends beyond the inner layer 20 to form an edge portion 40. The backing layer 30 and edge portion 40 contain the second adhesive. Referring to FIG. 6, together, the backing layer 30 and inner layer 20 form a thickened section of the barrier 10 that tapers down, at tapered section t, to the edge portion 40. In this manner, the barrier 10 is thicker around the stoma and thinner at the peripheral edges.

The barrier 10 further includes a barrier hole or opening 22, which is configured to be placed over a user's stoma, such that the stoma may extend through the opening 22 allowing the barrier 10 to be deployed. In embodiments, the opening 22 may range from 15 mm to 50 mm and is generally centered on the barrier 10. As will be appreciated, other opening sizes and placements may be employed if practical, and, in certain embodiments, such as the embodiment of FIGS. 7 and 8, an opening may not be provided. In such barriers, the opening may be created via a cutting tool prior to use.

Referring back to FIGS. 5 and 6, the barrier also includes a release layer 42, which further includes a pull tab 44. As will be appreciated, the pull tab 44 may be utilized to remove the release layer 42 such that the barrier 10 may be adhered.

In aspects of the invention, the first adhesive containing the high molecular weight polymeric buffer composition is located proximate to the stoma of a wearer, i.e., a first barrier surface. As such, the first adhesive provides for absorption of stoma effluent as well as pH regulation and erosion resistance in the peristomal area immediately adjacent to and surrounding a wearer's stoma. The second adhesive, which may contain a hydrocolloid, is utilized at the edge portion 40, i.e., a second barrier surface, which is at the outer periphery of the barrier 10. In this manner, the likelihood that the edge portion 40 will undesirably swell when contacted with water is reduced, as the second adhesive, e.g., a hydrocolloid based adhesive, has a lower absorptive capacity.

As discussed above, it is generally desirable that the first adhesive containing the high molecular weight polymeric buffer have an absorptive capacity of at least about 0.15 g/cm$^2$, but not to exceed 0.60 g/cm$^2$ as measured in the test of Example 1. In embodiments, the second adhesive, e.g., a hydrocolloid adhesive, has an absorptive capacity that is less than that of the first adhesive Continuing to refer to FIGS. 5-6, in a specific embodiment, the barrier 10 has a elliptical shape having a width of about 105 mm and a height of about 89 mm. The edge portion 40 is about 5 mm in width, and the tapered transition t between the backing and inner layer composite to the edge portion occurs over about a 2 mm span. The inner layer 20 containing the first adhesive has a thickness of about 0.4 mm and the backing layer 30 containing the second adhesive has a thickness of about 0.3 mm.

While embodiments are described in connection with an elliptical ostomy barrier having specific dimensions, the two or more adhesives of the present invention may be utilized with ostomy barriers and wound dressings of various shapes, sizes and layer thicknesses, e.g., annular, quadrilateral and other shapes may be employed. Moreover, the inner and backing layers 20, 30, need not be the same shape. For example, referring to FIGS. 7 and 8, in certain embodiments, the backing layer 130, which defines the overall form of the barrier 110, may be elliptical and the inner layer 120 may be round.

Figure 7:
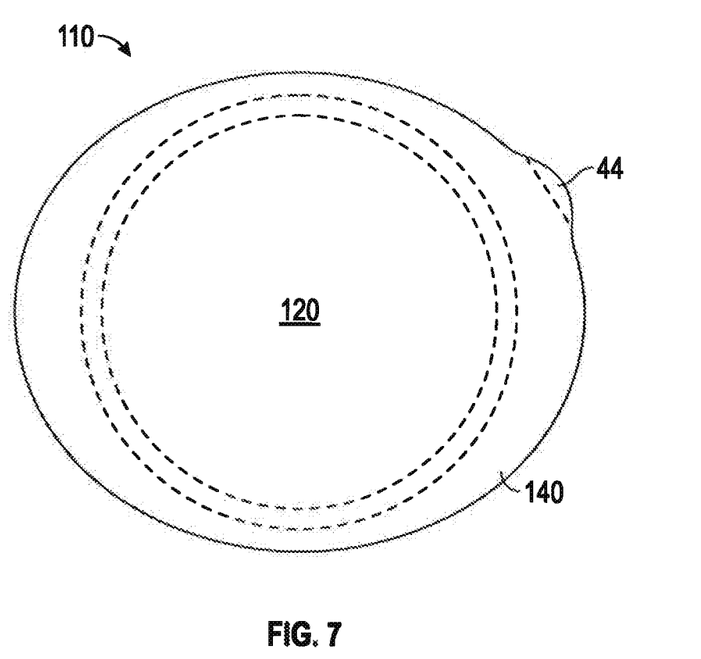
FIG. 7 illustrates an ostomy barrier according to another embodiment of the present invention.
Figure 8:
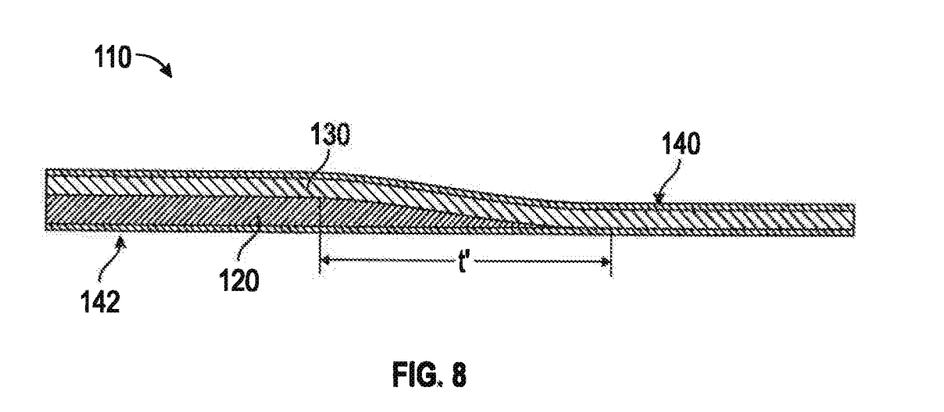
FIG. 8 illustrates a partial cross-sectioned view of the ostomy barrier of FIG. 7.

Continuing with FIGS. 7 and 8, in the depicted embodiment, the barrier 110 includes a round inner layer 120, containing the first adhesive, and an elliptical backing layer 130, which contains the second adhesive. Like the embodiment of FIGS. 5 and 6, the barrier 110 includes an edge portion 140, a release layer 142 and a tab 144 for removal of the release layer. In the depicted embodiment, the transition portion t' has a relatively large span of about 5 mm and the overall dimensions of the barrier are about 130 mm in width and 110 mm in height. The inner 120 and backing layers 130 are the same thickness as those in the embodiment of FIGS. 5 and 6.

Moreover, while the present invention has been described as having two adhesives, other embodiments may include three or more adhesives, each having different compositions and/or absorption/buffering capacities.

As will be appreciated, the adhesives need not overlay one another and may be placed on or form separate sections of an ostomy barrier or wound dressing without direct contact.

Embodiments of the invention may be manufactured through an injection molding process.

While the invention has been described with reference to the preferred embodiments, it will be understood by those skilled in the art that various obvious changes may be made, and equivalents may be substituted for elements thereof, without departing from the essential scope of the present invention. Therefore, it is intended that the invention not be limited to the particular embodiments disclosed.

What is claimed is:

1. An ostomy skin barrier comprising:
   a first adhesive that includes a polymeric buffer composition;
   a second adhesive, that includes a hydrocolloid; and
   wherein the first adhesive includes 40 wt. % of polyisobutylene, 16 wt. % of styrene-isoprene-styrene copolymer, 5 wt. % of liquid PIB, 4 wt. % of polyethylene fibers, 20 wt. % of cross linked polyacrylic acid, and 15 wt. % of cross linked partially neutralized polyacrylic acid.

2. The ostomy skin barrier of claim 1, wherein the second adhesive has a lower absorptive capacity than the first adhesive.

3. The ostomy skin barrier of claim 1, wherein the second adhesive includes 55.5 wt. % polyisobutylene, 14.5 wt. % of styrene-isoprene-styrene copolymer, 5 wt. % of polyethylene fibers, 8.3 wt. % of pectin, and 16.7 wt. % of CMC.

4. An ostomy skin barrier comprising:
   a first barrier surface having a first adhesive that includes a polymeric buffer composition; and
   a second barrier surface having a second adhesive includes a hydrocolloid; and
   wherein the first adhesive includes 40 wt. % of polyisobutylene, 16 wt. % of styrene-isoprene-styrene copolymer, 5 wt. % of liquid PIB, 4 wt. % of polyethylene fibers, 20 wt. % of cross linked polyacrylic acid, and 15 wt. % of cross linked partially neutralized polyacrylic acid.

5. The ostomy skin barrier of claim 4, wherein the first barrier surface is an inner layer formed from the first adhesive and the second barrier surface is a backing layer formed from the second adhesive, wherein the backing layer extends over and beyond the inner layer to form an edge portion of the barrier.

6. The ostomy skin barrier of claim 4, wherein the first barrier surface is configured to contact a peristomal area that is immediately adjacent to a wearer's stoma.

7. The ostomy skin barrier of claim 5, wherein the second adhesive has a lower absorptive capacity than the first adhesive reducing the likelihood that the edge portion will undesirably swell when contacted with a fluid.

8. The ostomy skin barrier of claim 4, wherein the first barrier surface includes a release layer.

9. A wound dressing comprising:
    a flexible outer layer;
    a first adhesive that includes a polymeric buffer composition
    a second adhesive that includes a hydrocolloid; and
    wherein the first adhesive includes 40 wt. % of polyisobutylene, 16 wt. % of styrene-isoprene-styrene copolymer, 5 wt. % of liquid PIB, 4 wt. % of polyethylene fibers, 20 wt. % of cross linked polyacrylic acid, and 15 wt. % of cross linked partially neutralized polyacrylic acid; and
    wherein the first and second adhesives are applied to a side of the flexible outer layer.

10. The wound dressing of claim 9, wherein the second adhesive has a lower absorptive capacity than the first adhesive.

11. A method of manufacturing an ostomy skin barrier comprising the steps of:
    forming a first adhesive into a first barrier surface, the first adhesive including a polymeric buffer composition; and
    forming a second adhesive that includes a hydrocolloid; and
    wherein the first adhesive includes 40 wt. % of polyisobutylene, 16 wt. % of styrene-isoprene-styrene copolymer, 5 wt. % of liquid PIB, 4 wt. % of polyethylene fibers, 20 wt. % of cross linked polyacrylic acid, and 15 wt. % of cross linked partially neutralized polyacrylic acid.

12. The method of claim 11, wherein the first adhesive has a higher absorptive capacity than the second adhesive.

* * * * *